United States Patent [19]

Marumoto et al.

[11] 4,258,033
[45] Mar. 24, 1981

[54] 2,6-DIAMINONEBULARINES

[75] Inventors: Ryuji Marumoto, Minoo; Masao Tanabe, Osaka; Yoshiyasu Furukawa, Shinsenriminami, all of Japan

[73] Assignee: Takeda Chemical Industries, Ltd., Osaka, Japan

[21] Appl. No.: 85,057

[22] Filed: Oct. 12, 1979

[30] Foreign Application Priority Data

Oct. 16, 1978 [JP] Japan .................. 53-127109
Jul. 9, 1979 [JP] Japan .................. 54-87074

[51] Int. Cl.³ ............... A61K 31/70; C07H 17/00; C07H 19/16
[52] U.S. Cl. ..................... 424/180; 536/24; 536/26
[58] Field of Search .............. 536/24, 26; 424/180

[56] References Cited

U.S. PATENT DOCUMENTS 3,936,439  2/1976  Marumoto et al. .................. 536/4

FOREIGN PATENT DOCUMENTS 42-10518  7/1967  Japan .
1390014  4/1975  United Kingdom .

Primary Examiner—Johnnie R. Brown
Assistant Examiner—Blondel Hazel
Attorney, Agent, or Firm—Wenderoth, Lind & Ponack

[57] ABSTRACT

Novel $N^2$-substituted phenyl-2,6-diaminonebularines of the formula

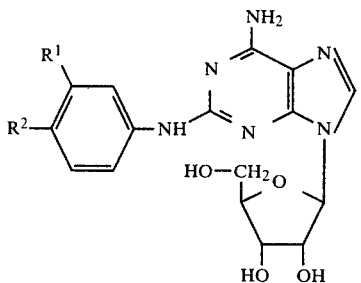

wherein either one of $R^1$ and $R^2$ is carbamoyl which may be substituted or acyl group and the other is hydrogen atom, halogen atom or lower alkoxyl group, and their acid addition salts have an excellent coronary vasodilator action.

11 Claims, No Drawings

2,6-DIAMINONEBULARINES

The present invention relates to novel $N^2$-substituted phenyl-2,6-diaminonebularines having excellent pharmacological action. More particularly, this invention relates to compounds of the formula,

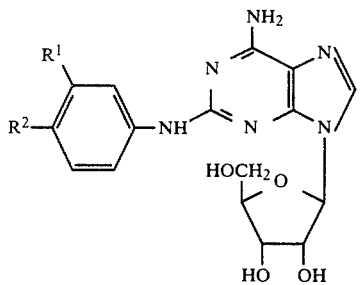

wherein either one of $R^1$ and $R^2$ is a group of the formula

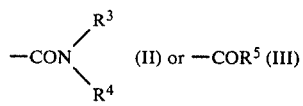

and the other is hydrogen atom, halogen atom or lower alkoxyl group, in the above formulas of II and III, $R^3$ is hydrogen atom or lower alkyl group; $R^4$ is hydrogen atom, lower alkyl group, cyclohexyl group or phenyl group and $R^5$ is lower alkyl group, or acid addition salts thereof, which have an excellent coronary vasodilator action.

Thus, the principal object of the present invention is to provide the novel 2,6-diaminonebularine derivatives (I) and their acid addition salts which show an excellent coronary vasodilator action, and another object is to provide pharmaceutical compositions comprising one or more of these compounds. A further object is to provide industrially feasible methods for producing these compounds. Other objects will be made clear from the description and claims presented hereinafter.

Referring to the above formula (I), either one of $R^1$ and $R^2$ is a group of the formula

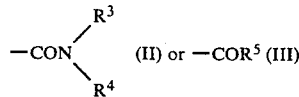

wherein $R^3$ is hydrogen atom or lower alkyl group, $R^4$ is hydrogen atom, lower alkyl group, cyclohexyl group or phenyl group and $R^5$ is lower alkyl group. The lower alkyl group for $R^3$, $R^4$ or $R^5$ in the formulas (II) and (III) may be a straight-chain or branched group and may, for example, be methyl, ethyl, n-propyl, isopropyl, n-butyl, t-butyl or hexyl group. The lower alkyl groups of up to 3 carbon atoms are particularly advantageous, while the other of $R^1$ and $R^2$ in the formula (I) is hydrogen-atom, halogen atom or lower alkoxyl group. The halogen atom may be any of chlorine, bromine and fluorine. The lower alkoxyl group may, for example, be methoxy, ethoxy, n-propoxy or isopropoxy. The lower alkoxyl groups of up to 3 carbon atoms are particularly preferred.

When one of $R^1$ and $R^2$ is a group of the formula (II), it is advantageous that $R^2$ is said group (II) and $R^1$ is hydrogen atom or halogen atom. When one of $R^1$ and $R^2$ is a group of the formula (III), it is preferable that $R^1$ is said group (III) and $R^2$ is hydrogen atom, halogen atom or lower alkoxyl group.

The above-mentioned compound (I) can be easily produced by for example, one of the following Process A and Process B.

Process A

A compound of the formula

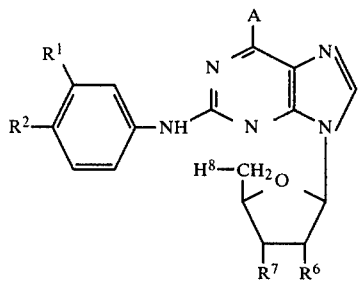

wherein $R^1$ and $R^2$ are as respectively defined hereinbefore; $R^6$, $R^7$ and $R^8$ each means hydroxyl group which may be protected and A is a reactive group capable of reacting with ammonia to yield an amino group, is reacted with ammonia and the resultant reaction product is, if necessary, deprotected to obtain a compound (I).

Referring to the above formula (IV), the protective groups for hydroxyls $R^6$, $R^7$ and $R^8$ may, for example, be acyl groups derived from carboxylic acids (e.g. aliphatic, aromatic or heterocyclic, saturated or unsaturated acyl groups such as acetyl, propionyl, caproyl, palmitoyl, benzoyl, toluoyl, furoyl, etc.), nitro, sulfonyl, isopropylidene, alkoxyalkylidene, etc., although acyl groups derived from aliphatic or aromatic carboxylic acids containing not more than 7 carbon atoms are preferred.

The hydroxyl groups $R^6$, $R^7$ and $R^8$ may all be protected, or only some of them, e.g. $R^6$ and $R^7$, may be protected. Or all of $R^6$, $R^7$ and $R^8$ may be unprotected hydroxyls. Normally protective groups on such protected hydroxyls are removed on reaction of (IV) with ammonia. However, in the case of groups which are difficult to remove by mere reaction with ammonia, such as benzoyl, toluoyl, nitro, sulfonyl or isopropylidene, can be easily removed by per se known procedures, e.g. by treatment with alkali metal in the case of benzoyl or toluoyl, by catalytic reduction in the case of nitro, or by treatment with acid (e.g. formic acid, acetic acid or hydrochloric acid, etc.) in the case of isopropylidene.

The reactive group A may be any group that is able to generate an amino group on reaction with ammonia. Thus, for example, halogen atom such as chlorine, bromine or iodine, or a group of the formula $-SO_nR^9$ ($R^9$ is hydrogen, alkyl or aralkyl; n is 0, 1 or 2), such as mercapto, alkylthio, aralkylthio, alkylsulfinyl, alkylsulfonyl, etc., may be employed with advantage.

In reacting the compound (IV) with ammonia in this Process A, it is generally advantageous to dissolve ammonia in a solvent and contact the solution with compound (IV). With respect to (IV), not less than equimolar amount, preferably about 2 to 5 molecular equivalents, of ammonia is preferably employed. The solvent may, for example, be a lower alkanol (e.g. methanol or ethanol), methyl-cellosolve or water, or a mixture thereof.

This reaction generally proceeds well at an elevated temperature of about 100° to 200° C., and is advantageously conducted in a sealed reaction vessel heating to the above-mentioned temperature. The above-mentioned starting compound (IV) can be prepared by the procedure described in U.S. Pat. No. 3,936,439 or any method analogous thereto.

Process B

A compound of the formula

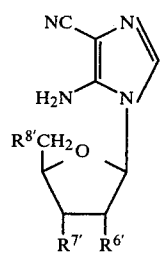

wherein $R^{6'}$, $R^{7'}$ and $R^{8'}$ each means a hydroxyl group which may optionally be protected, is reacted with a compound of the formula

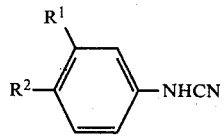

wherein $R^1$ and $R^2$ are as defined hereinbefore, and the reaction product is subjected, if necessary, to a deprotecting treatment to obtain the compound (I).

Referring to the above formula (IV), protective groups for the protected hydroxyls $R^{6'}$, $R^{7'}$ and $R^{8'}$ may be any of the groups mentioned in connection with $R^6$, $R^7$ and $R^8$ although propionyl is most advantageous. $R^{6'}$, $R^{7'}$ and $R^{8'}$ may all be protected hydroxyls, or only some of them, e.g. $R^{6'}$ and $R^{7'}$, may be protected. Or all of $R^{6'}$, $R^{7'}$ and $R^{8'}$ may be protected hydroxyls. While these hydroxyl protecting groups are normally removed on reaction of compound (V) with compound (VI), they can be, upon necessity, easily removed by per se known procedures, e.g. contacting the reaction product with a base (e.g. aqueous ammonia, alkali metal, etc.) in the case of acyl groups derived from carboxylic acids, by catalytic reduction in the case of nitro or by treatment with acid (e.g., formic acid, acetic acid, hydrochloric acid, etc.) in the case of isopropylidene.

The cyanamide compound of the above formula (VI) can be easily obtained, for example, by the method described in Berichte der Deutschen Chemischen Gesellschaft, 18, 3217–3234 (1885) or any method analogous thereto.

In reacting compound (V) with compound (VI) in Process B, it is generally advantageous to employ not less than equimolar amount, preferably about 2 to 5 molecular equivalents, of compound (VI) based on compound (V). Generally this reaction is preferably conducted in the presence of a base. As examples of the base may be mentioned ammonia, primary to tertiary amines (preferably low-boiling amines inclusive of cyclic amines, e.g. n-propylamine, isopropylamine, n-butylamine, triethylamine, pyridine, picoline, 2,6-lutidine, etc.), sodium or potassium alkoxides (e.g. sodium methoxide, sodium ethoxide, sodium methoxyethoxide, potassium tert-butoxide, etc.), or the like, although ammonia is particularly desirable. Normally, such a base may be advantageously employed in a proportion of about 10 to 100 molecular equivalents based on compound (V). Generally this reaction is preferably conducted in a solvent. The solvent may be any organic solvent that will not interfere with the reaction. Thus, for example, lower alkaonols (methanol, ethanol, propanol, etc.), tetrahydrofuran, dioxane, dimethylformamide, etc. as well as mixtures thereof, may be advantageously employed. Generally this reaction proceeds well under heating at about 100° to about 200° C., and is advantageously conducted in a sealed reaction vessel.

When the hydroxyl groups of the resultant compound still carry protective groups, the compound can be deprotected by the above-mentioned de-protecting procedure to obtain the compound (I).

The above starting compound (V) can, for instance, be easily produced in good yield from 5-amino-1-β-D-ribofuranosylimidazole-4-carboxamide which is readily available as an inexpensive fermentation product, in 2 or 3 steps by the method according to U.S. Pat. No. 3,450,693 or a modified method thereof.

From the reaction mixture, the desired $N^2$-substituted phenyl-2,6-diaminonebularine (I) can be easily isolated by procedures known per se. By way of example, compound (I) can be obtained in pure form by removing the excess reactants and solvent from the reaction mixture by distillation, and washing the residue with a lower alkanol and recrystallizing from water, a lower alkanol or a mixture thereof. The compound (I) may also be converted by a per se known procedure to a physiologically acceptable acid addition salt such as a mineral acid addition salt (hydrochloride, sulfate, etc.), and the salt so obtained be recovered.

The $N^2$-substituted phenyl-2,6-diaminonebularines (I) and salts thereof according to this invention are novel compounds and have excellent coronary vasodilator action, without side-effects such as hypotensive effect and being low in toxicity, and are of value, for example, as drugs for the treatment of ischemic heart diseases such as coronary insufficiency, angina pectoris, myocardial infarction and the like in mammalian animals [pet animals such as dog and cat; laboratory animals such as rat and mouse; and man, etc.] When the compound of this invention is used for such medicinal purposes, it can be orally or parenterally administered either as it is or in admixture with suitable pharmaceutically acceptable carriers, vehicles (or diluents, in such dosage forms as powders, granules, tablets, capsules, injections, etc. The dosage depends on the disease to be managed and the route of administration. However, the advantageous dosage for the treatment of coronary insufficiency in an adult human, for instance, is about 1 to 10 mg. daily by the oral route or about 0.05 to about 0.5 mg. daily by the intravenous route.

The following Examples, Reference Examples and Experiment are intended to further illustrate this invention and should by no means be construed as limiting the scope of the invention.

Throughout the foregoing description as well as in the following Examples, Reference Examples, Experiment and Claims, "μg.", "mg.", "g.", "kg.", "ml.", "l.", "°C.", "N" and "m.p." respectively refer to "microgram(s)", "milligrams(s)", "gram(s)", "kilogram(s)", "milliliter(s)", "liter(s)", "degree(s) centigrade", "Normal(s)" and "melting point".

REFERENCE EXAMPLE 1

In 200 ml of water was dissolved 34.5 g of 4-aminobenzamide hyrochloride, followed by addition of 25 g of potassium thiocyanate. The mixture was heated at 90° C. for 3 hours, whereupon 10 g. of 4-carbamoylphenylthiourea separated out. The crystals were suspended in 0.5 l. of a 10% aqueous solution of sodium hydroxide, and following addition of 50 g. of lead acetate, the suspension was stirred at room temperature for 20 minutes and further at 80° C. for 20 minutes. The precipitated lead sulfide was filtered off and the filtrate was neutralized with acetic acid. By the above procedure was obtained 3 g. of 4-carbamoylphenylcyanamide, m.p. 210°–212° C.

REFERENCE EXAMPLE 2

In 200 ml. of ethyl ether was suspended 25 g. of 3-aminobenzamide and, following addition of 25 g. of cyanogen bromide, the suspension was stirred for 3 hours. The precipitate was collected by filtration and washed with water. By the above procedure was obtained 13 g. of 3-carbamoylphenylcyanamide as crystals. m.p. 164°–166° C.

The above procedure was substantially repeated to obtain the N-(substituted phenyl)cyanamide compounds indicated in Table 1.

TABLE 1

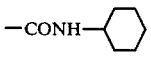

| R$^1$ | R$^2$ | Melting point (°C.) |
|---|---|---|
| —Cl | —CONH$_2$ | 168–170 |
| —H | —CONHCH$_3$ | 200–202 |
| —H | —CONHC$_2$H$_5$ | 171–173 |
| —H | —CONHC$_3$H$_7$ | 153–155 |
| —H | —CONH—⟨ ⟩ | 194–196 |
| —H | —CONH—⟨ ⟩ | 205–207 |
| —H | —CON(CH$_3$)$_2$ | 177–179 |
| —CONH—⟨ ⟩ | —H | 198–200 |

REFERENCE EXAMPLE 3

To the solution of 3-acetyl-4-ethoxyaniline hydrochloride 6 g. in water 100 ml. was added potassium thiocyanate 5 g., and the mixture was heated for 4 hours at 100° C. After cooling the precipitate was collected by filtration, dissolved in 10% aqueous potassium hydroxide solution 130 ml. To the solution was added lead acetate 19 g. and the mixture was stirred for 20 minutes at 80° C. The precipitated lead sulfide was filtered off and the filtrate was neutralized with acetic acid to obtain 1.9 g. of 3-acetyl-4-ethoxyphenylcyanamide m.p. 138°–139° C.

REFERENCE EXAMPLE 4

To the solution of 3-acetylaniline 13 g. in ethylether 100 ml. was added cyanogen bromide 20 g. and the mixture was stirred for 3 hours. The precipitate was filtered off and the filtrate was concentrated to dryness to give oily substance, which gradually crystalized. The crystals were pulverized and washed with water to give 6 g. of 3-acetylphenylcyanamide. m.p. 79°–81° C.

In the same manner as above, the phenylcyanamide derivatives given in Table 2 were obtained.

TABLE 2

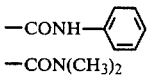

| R$^1$ | R$^2$ | Melting point (°C.) |
|---|---|---|
| —H | —COCH$_3$ | 152–154 |
| —COC$_2$H$_5$ | —H | 106–110 |
| —COC$_3$H$_7$ | —H | 70–74 |
| —OCH$_3$ | —COCH$_3$ | 162–163 |
| —Cl | —COCH$_3$ | 194–195 |

EXAMPLE 1

In an autoclave, 10 g. of 5-amino-1-β-D-ribofuranosyl-4-cyanoimidazole and 12 g. of 4-carbamoylphenylcyanamide were heated in 150 ml. of 20% methanolic ammonia at 180° C. for 5 hours. The reaction mixture was concentrated to dryness and the residue was washed with ethanol and recrystallized from 150 ml. of water. By the above procedure was obtained 2 g. of N$^2$-(4-carbamoylphenyl)-2,6-diaminonebularine, m.p. 277°–279° C. (decomposition).

| Elemental analysis | C(%) | H(%) | N(%) |
|---|---|---|---|
| Calculated (for C$_{17}$H$_{19}$O$_5$N$_7$) | 50.86 | 4.77 | 24.43 |
| Found | 50.10 | 4.77 | 24.35 |

EXAMPLE 2

2.5 g. of 5-amino-4-cyano-1-(2,3,5-tri-O-acetyl-β-D-ribofuranosyl)imidazole, 2.2 g. of 4-n-propylcarbamoylphenylcyanamide and 30 ml. of 20% methanolic ammonia were reacted and treated as in Example 1 to obtain 0.3 g. of N$^2$-(4-n-propylcarbamoylphenyl)-2,6-diaminonebularine, m.p. 167° C.

| Elemental analysis | C(%) | H(%) | N(%) |
|---|---|---|---|
| Calculated (for C$_{20}$H$_{25}$O$_5$N$_7$) | 54.16 | 5.68 | 22.11 |
| Found | 53.84 | 5.54 | 21.61 |

EXAMPLE 3

A mixture of 5 g. 2-bromoinosine ammonium salt, 8 g. 4-aminobenzamide and 60 ml. 60% aqueous methanol was refluxed for 5 hours and the crystal formed on cooling were collected by filtration. This procedure yields 3.2 g. of 2-(4-carbamoylphenylamino)inosine. The crystals were dissolved in 40 ml. of pyridine, 20 ml. of acetic anhydride was added and the mixture was allowed to stand at room temperature for 2 hours. It was then concentrated to dryness under reduced pressure and the residue was dissolved in 100 ml. of chloroform and dried over anhydrous sodium sulfate. To this chloroform solution were added 3 ml. of dimethylformamide and 3 ml. of phosphorus oxychloride under ice-cooling and refluxed for one hour. The reaction mixture was concentrated, the syrupy residue was decomposed with ice-water and extracted with 150 ml. of ethyl acetate. The extract was washed with water twice, with a saturated aqueous solution of sodium hydrogen carbonate and with water in that order and concentrated to dryness. By the above procedure was obtained 2-(4-carbamoylphenylamino)-6-chloro-2',3', 5'-tri-O-acetylnebularine as an oily residue. This oil was dissolved in 100 ml. of 20% methanolic ammonia and heated in an autoclave at 130° C. for 5 hours, after which it was concentrated to dryness. The residue was recrystallized from boiling water to obtain 0.5 g. crystals of $N^2$-(4-carbamoylphenyl)-2,6-diaminonebularine, m.p. 277°–279° C. (decomposition).

EXAMPLE 4 to 11

The compounds (I) indicated in Table 3 were obtained by following the same reaction and purification procedures as those described in Examples 1 to 3.

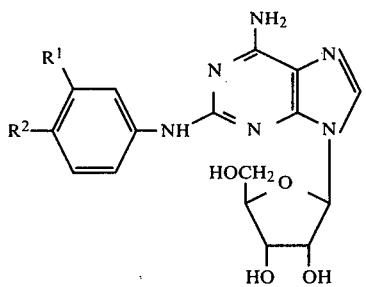

(I)

| Elemental analysis | C(%) | H(%) | N(%) | Cl(%) |
|---|---|---|---|---|
| Calculated (for $C_{10}H_{23}O_5N_7 \cdot HCl \cdot H_2O$) | 47.15 | 5.41 | 20.26 | 7.32 |
| Found | 46.87 | 5.24 | 19.01 | 7.14 |

EXAMPLE 13

In an autoclave, 2.4 g. of 5-amino-1-$\beta$-D-ribofuranosyl-4-cyanoimidazole, 2.6 g. of 3-propionylphenylcyanamide and 30 ml.. of 20% methanolic ammonia were heated for 5 hours at 180° C. The reaction mixture was concentrated to dryness and the residue was extracted with 700 ml. of hot water. The extract solution was cooled, whereupon was precipitated brown crystals, which were recrystallized from 300 ml. of hot water to give $N^2$-(3-propionylphenyl)-2,6-diaminonebularine as colorless needles, m.p. 148°–150° C.

| Elemental analysis | C(%) | H(%) | N(%) |
|---|---|---|---|
| Calculated (for $C_{19}H_{22}O_5N_6 \cdot \frac{1}{4}H_2O$) | 54.47 | 5.41 | 20.06 |
| Found | 54.36 | 5.22 | 20.15 |

EXAMPLE 14

2.5 g. of 5-amino-4-cyano-1-(2,3,5-tri-O-propionyl-$\beta$-D-ribofuranosyl)imidazole, 2.3 g. of 3-acetylphenylcyanamide and 30 ml. of methanolic ammonia were reacted and treated as in Example 13 to obtain 0.4 g. of $N^2$-(3-acetylphenyl)-2,6-diaminonebularine. m.p. 142°–143° C.

TABLE 3

| Example No. | $R^1$ | $R^2$ | Empirical formula | Elemental analysis* C(%) | H(%) | N(%) | Melting point (°C.) |
|---|---|---|---|---|---|---|---|
| 4 | —CONH$_2$ | —H | $C_{17}H_{19}O_5N_7$ | 50.86 | 4.77 | 24.43 | |
| | | | | 50.09 | 4.83 | 24.08 | 190–192 |
| 5 | —Cl | —CONH$_2$ | $C_{17}H_{18}O_5N_7Cl$ | 46.84 | 4.16 | 22.49 | |
| | | | | 46.52 | 4.47 | 22.15 | 258–260 |
| 6 | —H | —CONHCH$_3$ | $C_{18}H_{21}O_5N_7 \cdot H_2O$ | 49.88 | 5.34 | 22.62 | |
| | | | | 49.79 | 5.39 | 22.55 | 170–173 |
| 7 | —H | —CONHC$_2$H$_5$ | $C_{19}H_{23}O_5N_7 \cdot \frac{1}{2}H_2O$ | 52.04 | 5.51 | 22.36 | |
| | | | | 52.03 | 5.81 | 22.11 | 171–173 |
| 8 | —H | —CONH—⟨⟩ | $C_{23}H_{29}O_5N_7 \cdot 2H_2O$ | 53.17 | 6.40 | 18.87 | |
| | | | | 53.66 | 6.35 | 18.60 | 168–169 |
| 9 | —H | —CONH—⟨⟩ | $C_{23}H_{23}O_5N_7$ | 57.85 | 4.85 | 20.53 | |
| | | | | 57.84 | 4.92 | 19.97 | 267–268** |
| 10 | —H | —CON(CH$_3$)$_2$ | $C_{19}H_{23}O_5N_7 \cdot H_2O$ | 51.00 | 5.63 | 21.91 | |
| | | | | 50.96 | 5.55 | 21.78 | 177–178 |
| 11 | —CONH—⟨⟩ | —H | $C_{23}H_{23}O_5N_7$ | 57.85 | 4.85 | 20.53 | |
| | | | | 57.87 | 4.76 | 20.32 | 202–204 |

*Calculated values in each top row; found values in each bottom row.
**Decomposition point.

EXAMPLE 12

In 20 ml. of water was suspended 2.8 g. of $N^2$-(4-ethylcarbamoylphenyl)-2,6-diaminonebularine, which was dissolved completely with 6.5 ml. of 1N-HCl. The solution was allowed to stand in the cold, whereupon 2.2 g. of $N^2$-(4-ethylcarbamoylphenyl)-2,6-diaminonebularine.hydrochloride was obtained as fine colorless crystals, m.p. 167°–169° C. (decomposition).

| Elemental analysis | C(%) | H(%) | N(%) |
|---|---|---|---|
| Calculated (for $C_{18}H_{20}O_5N_6$): | 53.99 | 5.04 | 20.99 |
| Found | 53.23 | 5.19 | 19.75 |

EXAMPLE 15

A mixture of 3 g. of 2-bromoinosine ammonium salt, 5 g. 3-acetylaniline and 50 ml. of 60% aqueous methanol was refluxed for 10 hours. After cooling, the precipitate was collected to give 2.2 g. of 2-(3-acetylphenylamino)-inosine. The crystals were dissolved in 30 ml. of pyridine. To the solution was added 15 ml. of acetic anhydride, and the mixture was allowed to stand at room temperature for 2 hours. The mixture was concentrated to dryness in vacuo and the resulting syrupy residue was dissolved in 70 ml. of chloroform and dried over anhydrous sodium sulfate. To the chloroform solution were added 2 ml. of dimethylformamide and 2 ml. of phosphorus oxychloride under ice-cooling and refluxed for one hour. The reaction mixture was concentrated, and the residue was decomposed with ice-water, followed by extraction with 100 ml. of water. The extract was washed with water and concentrated to give oily 2-(3-acetylphenylamino)-6-chloro-2',3',5'-tri-O-acetyl-nebularine. The oily substance was dissolved in 50 ml. of 20% methanolic ammonia and heated for 5 hours at 120° C. in an autoclave. The reaction mixture was concentrated to dryness and the residue was recrystallized from hot water to give 0.32 g. of $N^2$-(3-acetylphenyl)-2,6-diaminonebularine as crystals. m.p. 142°–143° C.

EXAMPLE 16 to 20

The compounds (I) described below in Table 4 were obtained by the reaction and purification procedures similar to those set forth in Example 13 to 15.

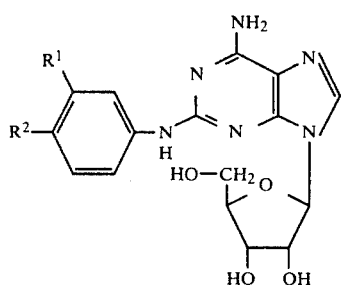

TABLE 2

| Example No. | $R^1$ | $R^2$ | Molecular formula | Elemental analysis* C(%) | H(%) | N(%) | Melting point (°C.) |
|---|---|---|---|---|---|---|---|
| 16 | —H | —COCH$_3$ | C$_{18}$H$_{20}$O$_5$N$_6$ | 53.99 53.81 | 5.04 4.95 | 20.99 21.10 | 252–253 |
| 17 | —COCH$_3$ | —OC$_2$H$_5$ | C$_{20}$H$_{24}$O$_6$N$_6$ · ½H$_2$O | 52.97 53.03 | 5.56 5.40 | 18.53 18.57 | 128–129 |
| 18 | —COC$_3$H$_7$ | —H | C$_{20}$H$_{24}$O$_5$N$_6$ | 56.06 55.79 | 5.65 5.44 | 19.62 19.25 | 204–205 |
| 19 | —OCH$_3$ | —COCH$_3$ | C$_{19}$H$_{22}$O$_6$N$_6$ · ½H$_2$O | 51.93 52.06 | 5.27 5.24 | 19.12 19.24 | 225–226 |
| 20 | —Cl | —COCH$_3$ | C$_{18}$H$_{19}$O$_5$N$_6$Cl | 49.71 49.53 | 4.40 4.19 | 19.33 19.57 | 194–195 |

*Calculated values in each top row, found values in each bottom rows.

EXAMPLE 21

In 20 ml. of water was suspended 0.5 g. of $N^2$-(4-acetylphenyl)-2,6-diaminonebularine, which was dissolved completely with 2 ml of 1N-HCl. The solution was allowed to stand in the cold, whereupon 0.6 g. of 2-(4-acetylphenyl)-2,6-diaminonebularine hydrochloride separated as fine colorless needles, m.p. 208°–210° C. (decomposition).

| Elemental analysis | C(%) | H(%) | N(%) | Cl(%) |
|---|---|---|---|---|
| Calculated (for C$_{18}$H$_{20}$O$_5$N$_6$ · | 49.48 | 4.84 | 19.24 | 8.11 |

| Elemental analysis | C(%) | H(%) | N(%) | Cl(%) |
|---|---|---|---|---|
| HCl) Found | 49.12 | 4.97 | 18.96 | 8.02 |

EXAMPLE 22

For the treatment of ischemic heart diseases such as coronary insufficiency, angina pectoris, myocardial infarction, etc., the compound (I) of this invention can be administered in the following dosage forms.

| 1. | Tablets | |
|---|---|---|
| (1) | $N^2$-(4-carbamoylphenyl)-2,6-diaminonebularine | 1 mg. |
| (2) | Lactose | 35 mg. |
| (3) | Corn starch | 150 mg. |
| (4) | Microcrystalline cellulose | 30 mg. |
| (5) | Magnesium stearate | 5 mg. |
| | | 221 mg. per tablet |

The entie amounts of (1), (2) and (3), ⅔ of (4) and ½ of (5) are admixed and granulated. To the granules are added the remainders of (4) and (5) and the entire composition is compression-molded into a tablet.

| 2. | Capsules | |
|---|---|---|
| (1) | $N^2$-(3-acetylphenyl)-2,6-diaminonebularine | 1 mg. |
| (2) | Lactose | 100 mg. |
| (3) | Microcrystalline cellulose | 70 mg. |
| (4) | Magnesium stearate | 10 mg. |
| | | 181 mg. per capsule |

The entire amounts of (1), (2) and (3) and ½ of (4) are admixed and granulated. The remainder of (4) is added and the entire composition is sealed into a gelatin capsule.

| 3. | Injectable solution | |
|---|---|---|
| (1) | $N^2$-(4-ethylcarbamoylphenyl)-2,6-diaminonebularine hydrochloride | 0.1 mg. |
| (2) | Inositol | 100 mg. |
| (3) | Benzyl alcohol | 20 mg. |

The entire amounts of (1), (2) and (3) are dissolved in a sufficient amount of distilled water for injection to make 2 ml. and the solution is sealed into a brown-colored ampoule container, followed by purging with nitrogen gas. The whole procedure is aseptically performed.

Experiment

Dogs weighing 7 to 12 kg. were anaesthetized with pentobarbital sodium (30 mg/kg, intravenous) and, under supportive respiration, a left thoractomy was performed at the fifth intercostal space to expose the heart. An extracorporeal blood circuit was established between the femoral artery and the left coronary arterial ciroumflex via a polyethylene tube. The coronary blood flow was measured with an electromagnetic flow-meter disposed along the extracorporeal circuitry.

The test compound, as a 1 µg/ml. solution in physiological saline, was administered directly into the coronary artery through the polyethylene tube at the dose of 0.1 µg/dog, and the coronary arterial flow were measured at 30 seconds, one minute, 2 minutes, 3 minutes and 5 minutes following the administration. The results are shown in Table 5. The percent increases in coronary arterial flow were calculated by means of the following equation.

$$\frac{\text{Coronary blood flow at each time point after using} - \text{coronary blood flow before dosing}}{\text{Coronary blood flow before dosing}} \times 100 =$$

Percent increase in coronary blood flow

TABLE 5

| Compound | \multicolumn{5}{c}{Percent increase in coronary blood flow After dosing} | | | | |
| --- | --- | --- | --- | --- | --- |
| | 30 seconds | 1 minute | 2 minutes | 3 minutes | 5 minutes |
| $N^2$-(4-Carbamoylphenyl)-2,6-diaminonebularine | 199.0 | 70.3 | 17.0 | 2.0 | — |
| $N^2$-(3-Carbamoylphenyl)-2,6-diaminonebularine* | 231.1 | 41.9 | 21.0 | 27.9 | 17.1 |
| $N^2$-(4-Methylcarbamoyl-phenyl)-2,6-diaminonebularine | 152.5 | 65.6 | 18.0 | 20.6 | 6.9 |
| $N^2$-(4-Ethylcarbamoyl-phenyl)-2,6-diaminonebularine | 173.2 | 99.7 | 9.5 | 9.3 | — |
| $N^2$-(4-n-Propylcarbamoyl-phenyl)-2,6-diaminonebularine | 237.8 | 127.3 | 9.2 | 19.2 | 9.1 |
| $N^2$-(4-Dimethylcarbamoyl-phenyl)-2,6-diaminonebularine | 295.7 | 142.9 | 20.7 | 7.2 | 0 |
| $N^2$-(4-Cyclohexyl-carbamoylphenyl)-2,6-diaminonebularine | 237.2 | 191.5 | 68.6 | 27.2 | 3.6 |
| $N^2$-(4-Acetylphenyl)-2,6-diaminonebularine | 269.5 | 201.5 | 47.5 | 17.1 | 7.6 |
| $N^2$-(3-Acetylphenyl)-2,6-diaminonebularine | 295.0 | 85.9 | 36.7 | 32.5 | 18.4 |
| $N^2$-(3-Propionylphenyl)-2,6-diaminonebularine | 284.2 | 115.0 | 73.5 | 58.6 | 35.9 |
| $N^2$-(3-n-Butyrylphenyl)-2,6-diaminonebularine | 279.0 | 142.1 | 61.9 | 43.7 | 25.4 |
| $N^2$-(4-Ethoxy-3-acetyl-phenyl)-2,6-diamino-nebularine | 277.8 | 127.9 | 61.1 | 41.8 | 26.3 |

*0.3 µg./dog.

What is claimed is:

1. A compound of the formula:

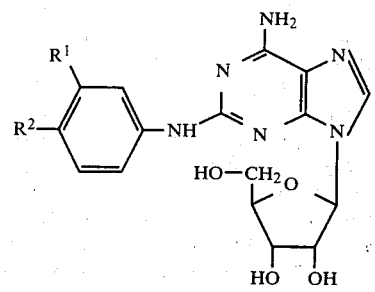

wherein one of $R^1$ and $R^2$ is of the formula:

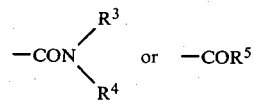

and the other is hydrogen, halogen or lower alkoxyl in the above formulas, $R^3$ is hydrogen or lower alkyl; $R^4$ is hydrogen, lower alkyl, cyclohexyl or phenyl and $R^5$ is lower alkyl or an acid addition salt thereof.

2. A compound according to claim 1, wherein one of $R^1$ and $R^2$ is of the formula:

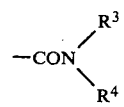

and the other is hydrogen or halogen.

3. A compound according to claim 2, wherein $R^2$ is of the formula:

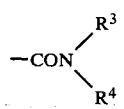

and $R^1$ is hydrogen.

4. A compound according to claim 3, wherein each of $R^3$ and $R^4$ is lower alkyl.

5. A compound according to claim 1, wherein one of $R^1$ and $R^2$ is of the formula:

—COR$^5$ and the other is hydrogen, halogen or lower alkoxyl.

6. A compound according to claim 5, wherein $R^1$ is of the formula

—COR$^5$ and $R^2$ is hydrogen.

7. A compond according to claim 1, wherein the acid addition salt is a mineral acid addition salt.

8. A compound according to claim 1, said compound being $N^2$-(4-dimethylcarbamoylphenyl)-2,6-diaminonebularine.

9. A compound according to claim 1, said compound being $N^2$-(3-acetylphenyl)-2,6-diaminonebularine.

10. A pharmaceutical composition which contains an effective amount for the treatment of ischemis heart diseases in mammals of a compound of the formula:

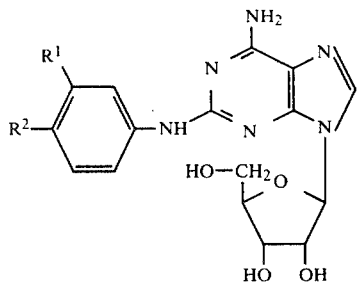

wherein one of $R^1$ and $R^2$ is of the formula:

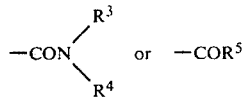

and the other is hydrogen, halogen or lower alkoxyl in the above formulas, $R^3$ is hydrogen or lower alkyl; $R^4$ is hydrogen, lower alkyl, cyclohexyl or phenyl and $R^5$ is lower alkyl or an acid addition salt thereof, and a pharmaceutically acceptable carrier, vehicle or diluent therefor.

11. A method for the treatment of ischemic heart diseases in mammal, which comprises administering to the mammal an effective amount of a compound of the formula:

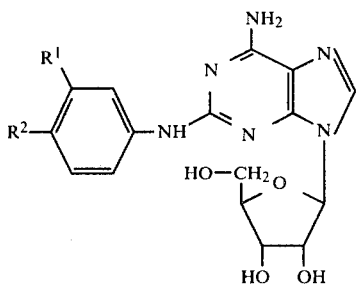

wherein one of $R^1$ and $R^2$ is of the formula:

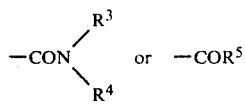

and the other is hydrogen, halogen or lower alkoxyl in the above formulas, $R^3$ is hydrogen or lower alkyl; $R^4$ is hydrogen, lower alkyl, cyclohexyl or phenyl and $R^5$ is lower alkyl, or an acid addition salt thereof.

* * * * *